United States Patent [19]
Alburger

[11] 3,935,731
[45] Feb. 3, 1976

[54] METHOD AND MEANS FOR IMPROVING FLAW ENTRAPMENT EFFICIENCY IN WATER-WASHABLE INSPECTION PENETRANTS

[76] Inventor: James R. Alburger, 5007 Hillard Ave., La Canada, Calif. 91011

[22] Filed: Feb. 28, 1975

[21] Appl. No.: 554,084

Related U.S. Application Data

[63] Continuation-in-part of Ser. No. 163,643, July 19, 1971, abandoned, which is a continuation of Ser. No. 875,552, Nov. 10, 1969, abandoned, which is a continuation-in-part of Ser. No. 590,353, Oct. 28, 1966, abandoned.

[52] U.S. Cl............. 73/104; 106/19; 252/301.2 P; 427/8
[51] Int. Cl.² ............... G01N 29/04; G01N 13/02
[58] Field of Search ............... 252/62.52, 301.2 P; 106/20, 19; 73/104; 427/8

[56] References Cited
UNITED STATES PATENTS

| | | | |
|---|---|---|---|
| 2,764,556 | 9/1956 | Sockman et al. | 106/19 |
| 3,386,920 | 6/1968 | Alburger | 252/301.2 |
| 3,558,882 | 12/1968 | Mlot-Fijaikowski | 252/408 |

*Primary Examiner*—Theodore Morris

[57] ABSTRACT

An improvement in inspection penetrant processes for the detection of surface defects in test bodies, wherein a water-washable penetrant of the balanced surfactant/synergist type or of the slow-solubility type is inhibited with respect to its solubility in wash water to the point of substantial insolubility except in the presence of mechanical agitation or application of a vigorous spray of wash water, thereby enhancing the flaw entrapment efficiency of penetrant indications. The inhibition or depression of solubility is achieved by any one or a combination of several techniques; (1) raising the temperature of the wash water to above a critical point of solubility inversion, (2) dissolving a solubility-inhibiting solute in the wash water or in the penetrant, and (3) allowing a solubility-producing constituent to evaporate from the penetrant.

2 Claims, 4 Drawing Figures

INVENTOR.
James R. Allburger

METHOD AND MEANS FOR IMPROVING FLAW ENTRAPMENT EFFICIENCY IN WATER-WASHABLE INSPECTION PENETRANTS

This application is a continuation-in-part of application Ser. No. 163,643, filed July 19, 1971 now abandoned, for "Method and Means for Improving Flaw Entrapment Efficiency in Water-Washable Inspection Penetrants", now abandoned, which application was a continuation of application Ser. No. 875,552, filed Nov. 10, 1969, for "Method and Means for Improving Flaw Entrapment Efficiency in Water-Washable Inspection Penetrants", now abandoned, which application was a continuation-in-part of appln. Ser. No. 590,353, filed Oct. 28, 1966, for "Method and Means for Improving Flaw Entrapment Efficiency in Water-Washable Penetrants", now abandoned. The invention relates to a method and means for improving flaw entrapment stability in water-washable penetrants. More particularly, the invention relates to a method and means of wash-removal of water-washable penetrants and emulsifiers in which there is a reduced tendency for removal of desired flaw entrapments of penetrant.

RELATED PATENTS AND PATENT APPLICATIONS

U.S. Pat. No. 3,164,006 for "Evaluation Performance of Liquid Penetrant Tracer Materials."

U.S. Pat. No. 3,282,843 for "Emulsifier Compositions".

U.S. Pat. No. 3,311,479 for "Penetrant Inspection Process and Compositions".

U.S. Pat. No. 3,349,041 for "Gel-Forming Inspection Penetrant and Emulsifier Compositions and Processes."

U.S. Pat. No. 3,422,670 for "Cleaning Process and Compositions for Post-Emulsifier Inspection Penetrants."

U.S. Pat. No. 3,429,826 for "Gel-Forming Inspection Penetrant and Emulsifier Compositions Employing Hydrophilic and Lipophilic Surfactants."

Reissue No. 26,888 for "Process for Fluorescence Detection of Extremely Thin Tracer Films" (Formerly U.S. Pat. No. 3,386,920).

Appln. Ser. No. 787,381, filed Dec. 27, 1968 for "Oil-Water Compatible Compositions and Methods for Preparing Same."

Appln. Ser. No. 804,200, filed Mar. 4, 1969 for "Oil-Water Compositions Employing Non-Surface-Active Constituents".

Appln. Ser. No. 224,656, filed Feb. 9, 1972, for "Inspection Penetrant Process and Composition for Aiding Removal of Excess Penetrant from Test Part Surfaces", now U.S. Pat. No. 3,751,970.

Appln. Ser. No. 482,465, filed June 24, 1974, for "Enhanced Stability Water-Washable Penetrant Composition and Process", now U.S. Pat. No. 3,896,664.

DETAILED SPECIFICATION

Water-washable penetrants are well known in the art, and they usually comprise an oily carrier containing an indicator dye and a suitable detergent system which renders the oily liquid emulsifiable, soluble, or otherwise washable in water. Materials of this kind are known as "self-emulsifiable penetrants". Emulsifiers, as used in the inspection penetrant process, are essentially the same as water-washable penetrants, except that the emulsifiers are employed in a separate process step following the application to test bodies of a water-insoluble oily penetrant containing an indicator dye. The combination of a normally insoluble penetrant and a separate emulsifier is known as a "post-emulsifier system", and the penetrant and emulsifier, when blended together, become in effect a water-washable penetrant. In all cases, the water-washable penetrant, or the insoluble oily penetrant which has been "emulsified" by contact with an emulsifier, as the case may be, and which is present on the surface of test bodies, is removed by the application of a water wash or rinse in such a way that surface penetrant (and emulsifier) is removed, leaving flaw entrapments of dyed penetrant which can subsequently be detected in an inspection step.

For the purpose of the following specification, the terms "water-washable penetrant" and "emulsifier" are used interchangeably, and such materials are considered to be equivalent; that is, for the purpose of inspection penetrant processes. Both visible-color dyes and fluorescent dyes and commonly employed as indicators in these penetrants. At least one indicator dye is always used in inspection penetrant materials as employed in connection with this invention, and these dyes may be present in the water-washable penetrant, or they may be present in an oily water-insoluble penetrant which is subsequently rendered water-washable by contact with an emulsifier.

Any suitable indicator dye may be employed, such dyes being well known in the art. Many kinds of visible-color dyes are available for such usage, most of these being of the oil-soluble types. Where fluorescent dyes are to be utilized, the preferred types are those which are described in my U.S. Pat. No. 3,386,920, now Reissue No. RE-26,888.

Inasmuch as water-washable penetrants and emulsifiers are, by their very nature, soluble in water, a prolonged washing with water will tend to remove the soluble or emulsified penetrant from flaw entrapments to a degree which may seriously affect the flaw detection capability of the inspection penetrant system. In some cases, it is possible to minimize the unwanted stripping of the soluble or emulsified penetrant from surface defects by employing a carefully controlled and short washing time. However, in other cases, particularly where large test bodies are being treated in the inspection penetrant process, it is difficult or even impossible to control the washing time to a sufficiently short period, with the result that over-washing may take place.

In the so-called post-emulsifier system of penetrant inspection, in which there is employed a water-insoluble penetrant and a separate emulsifier, the emulsifier usually diffuses into penetrant entrapments in shallow surface flaws to a considerable degree, rendering large portions of such entrapments soluble in water. Then, any condition of over-washing will tend to remove an excessive amount of the entrapped penetrant, thereby reducing the effectiveness of the flaw detection process.

I have found that it is possible, in certain penetrant materials, to alter the rate at which the "soluble" or emulsified penetrant is washed from test bodies during the washing step, and thereby minimize the loss of desired indications. In some cases, I have found it possible to render the normally soluble or water-washable penetrant (or emulsifier) quite insoluble in the wash medium, yet removable to a controllable degree by means of mechanical agitation, or by what I call a spray-scrubber, or scrubber action. The thus-insolubilized penetrant material is thereby made to yield a high level of flaw entrapment efficiency or stability.

This invention contemplates a method for wash-removal of emulsified, self-emulsifiable, or soluble surface penetrant, wherein the solubility of the penetrant is partially inhibited, either by treating the wash water or by adjusting the solubility characteristic of the penetrant or emulsifier itself, such that solubility is reduced to a substantial degree for washing conditions corresponding to a gentle flow of wash water. Then, washing is carried out by employing a mechanical agitation, or spray-scrubber action, along with the application of the wash water, the agitation serving to accelerate any residual degree of solubility of the surface penetrant. It will be understood that the mechanical agitation or spray-scrubber action referred to herein may be induced by means of air-agitation of the wash water, or by rapid circulation of the wash water to provide movement of the wash water over surfaces of test parts which are immersed in the wash water. Due to the fact that entrapments of penetrant in surface flaws are not subjected to the mechanical agitation, as is the surface penetrant, the flaw entrapments are not removed, or at least are removed relatively slowly. The result of employing this inhibition or depression of solubility, along with mechanical agitation during washing, is that penetrant indications of small, shallow surface flaws are retained to a high degree of entrapment efficiency.

The principal object of this invention, therefore, is to provide a method and means for improving flaw entrapment stability in water-washable penetrants and emulsifiers.

Another object of the invention is to provide processes and compositions for wash removal of surface penetrant in which there is a reduced tendency to strip penetrant entrapments from surface flaws.

Still another object of the invention is to provide improved wash techniques and materials for an inspection penetrant process, whereby a tendency toward over-washing may be minimized and may be controlled.

A further object of the invention is to provide improved materials and techniques for wash-removal of emulsified penetrant material from test objects which permit increased latitude in washing time.

Other and incidental objects of the invention will in part be obvious and will in part become apparent from the following specification and drawings, in which.

Figure 1:
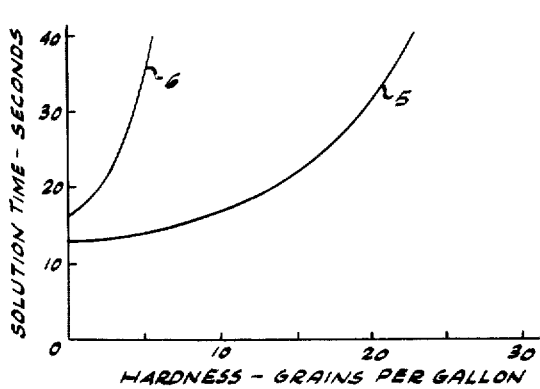
FIG. 1 is a graph in which the time for wash-removal of certain penetrant materials is plotted against the degree of hardness of the wash water.

Conventional emulsifier or self-emulsifiable oily compositions usually consist of mixtures of an oil, such as a light oil or kerosene, with an appropriate detergent which is capable of simultaneously coupling with the oil and with water. There are many kinds of detergent materials which will behave in this manner, most of them being water soluble "surface active" agents. In general, these materials may be categorized as ionic (anionic or cationic) detergents, or nonionic detergents. Many of the ionic-type detergents may be in the form of fatty acid soaps. When a self-emulsifiable oily composition is used as a water-washable penetrant, a dye indicator is dissolved in the composition. One important characteristic of water-washable inspection penetrants is that the emulsifiable composition is usually capable of tolerating a certain amount of added water without clouding, gelling, or separation of constituents.

According to the present understanding of the mechanism involved in wash removal of a layer of emulsifiable oily liquid, water applied to the layer first enters the layer, forming a clear mixture of water and emulsifiable oil. This clear mixture consists of clusters of complexes of molecular groups, known as micelles, in which molecules of water and oil are attached to molecular groupings of surfactant (detergent) material in more-or-less stable structures. As more water enters these molecular complexes, they tend to enlarge and change their form, passing through several partial inversions or structural changes, these changes being observable by the formation of a haze in the mixture and by sharp changes in viscosity at the points of transition or partial inversion.

When the amount of water which enters the emulsifiable oil is beyond a certain critical point, the micelles become unstable and the mixture undergoes a final inversion and breaks into a milky emulsion. As a result of the above-described mechanism, the emulsified material becomes separated from the surface to which it had been applied, and may be rinsed off of the surface and flushed away.

The above-described mechanism of solvency applies generally to all self-emulsifiable oil-surfactant compositions. However, I have found that the sensitivity of a given emulsifiable composition to the application of various techniques of solvency inhibition may vary somewhat, depending on the type of surfactant system which is employed.

Certain of the conventional emulsifiers, or self-emulsifiable water-washable penetrants, utilize ionic surfactant constituents, and these may be anionic or cationic in nature. Fatty acid soaps, which are anionic in nature, are frequently employed as emulsifying agents. Compositions of these kinds may be solvency-sensitive to the presence of hardness-producing metal ions in the wash water.

I have discovered that there is an important class of self-emulsifiable penetrant and emulsifier compositions, the members of which exhibit exceptional solvency-sensitivity in a number of ways which will be described. This class of compositions includes emulsifiers and water-washable penetrants disclosed and claimed in my U.S. Pat. Nos. 3,282,843, 3,349,041, and 3,429,826, and my copending applications Ser. Nos. 787,381, filed Dec. 27, 1968, for "Oil-Water Compatible Compositions and Methods for Preparing Same", and 804,200, filed Mar. 4, 1969, for "Oil-Water Compatible Compositions Employing Non-Surface-Active Constituents".

All of the emulsifier and water-washable penetrant compositions in this class have one unique feature in common, this being the fact that the detergent system employed consists essentially of a balanced mixture of a water-compatible (hydrophilic) surface-active constituent, known as a "surfactant", and an oil-compatible (lipophilic) constituent, known as a "synergist".

In constructing a water-compatible gel-forming oily composition containing a detergent system of the balanced surfactant/synergist type, one practical method is to add a water-soluble surface-active constituent (surfactant) to an oil ingredient in an amount sufficient to cause a haze or separation to form in the mixture. Then, a synergist constituent is added in an amount sufficient to clear the haze and form a homogeneous transparent mixture. If this procedure is carried out properly, as taught in my above-mentioned copending application, Ser. No. 787,381, the resulting oil-surfactant-synergist mixture will tolerate the addition of water, and will exhibit distinctive gel-forming or emulsion-forming properties.

It will be understood that "balanced" mixtures of surfactant and synergist materials may be prepared without the presence of either oil or water constituents, and these compositions will have the property of being simultaneously compatible with oil and water. In accordance with the teachings of my above-mentioned patents and patent applications, a "surfactant" constituent may be any member of the following group of water-soluble, oil-incompatible surface-active materials.

Ethoxylated alkylphenols (7 to 30 mols ethylene oxide);
Ethoxylated diamylphenol,
Ethoxylated octylphenol,
Ethoxylated nonylphenol
Ethoxylated dinonylphenol,
Ethoxylated trinonylphenol,
Ethoxylated decylphenol,
Ethoxylated didecylphenol,
Ethoxylated undecylphenol,
Ethoxylated dodecylphenol
Ethoxylated octyldecylphenol,
Ethoxylated diamylnaphthol,
Ethoxylated octylnaphthol,
Ethoxylated nonylnaphthol,
Ethoxylated dinonylnaphthol,
Ethoxylated trinonylnaphthol,
Ethoxylated octyldecylnaphthol,
Ethoxylated diamyl p-p' biphenol,
Ethoxylated octyl p-p' biphenol,
Ethoxylated nonyl p-p' biphenol,
Ethoxylated dinonyl p-p' biphenol,
Pyrrolidone and pyrrolidone derivitives,
2-Pyrrolidone,
N-Methyl pyrrolidone,
N-Vinyl pyrrolidone,
Esterified pyrrolidones,
Dimethyl formamide,
Oil-insoluble glycols,
Triethylene glycol,
Diethylene glycol,
Polyethylene glycol,
Water-insoluble polypropylene glycols,
Polyhydric alcohols,
Glycerin,
Ethoxylated octyldecyl p-p' biphenol,
Polyoxyalkylene derivitives of hexitol anhydride,
Sorbitol esters of fatty acids,
Polyoxyalkylene ethers,
Alkyl aryl polyether alcohols,
Polyoxyalkylene esters of organic acids,
Ethoxylated fatty esters,
Ethoxylated alcohols,
Ethoxylated amines,
Ethoxylated polyoxy propylene glycols (Pluronics),
Ethoxylated phosphate esters,
Ethoxylated amides,
Ethoxylated fatty acids,
Monoglyceride derivitives,
Alkanolamides,
Fatty esters,
Sulfonated oils,
Sulfonated amides,
Sulfonated amines,
Alkyl sulfonates,
Diphenyl sulfonate derivitives,
Polyoxyalkylene thioethers,
Polyoxyalkylene fatty amides,
Polyoxyalkylene sorbitan monolaurate,
Polyoxyalkylene sorbitan monostearate,
Polyoxyalkylene sorbitan monopalmitate,
Polyoxyalkylene sorbitan tristearate,
Polyoxyalkylene sorbitan monooleate,
Polyoxyalkylene sorbitan trioleate,
Polyoxyalkylene sorbitol laurate,
Polyoxyalkylene sorbitol hexoleate,
Polyoxyalkylene septaoleate,
Polyoxyalkylene oleate-laurate,
Polyoxyalkylene ester of mixed fatty and resin acid,
Polyoxyalkylene Ether alcohol, It will be noted that certain of the above-identified surfactants are nonionic in character, while others are ionic in nature, and that some of these ionic surfactants may be classed as fatty acid soaps. Also, in accordance with the teachings of the above-mentioned patents and patent applications, a "synergist" may be any member of the following group of oil-compatible water-insoluble substances.

Ethoxylated alkylphenols (zero to 5 mols ethylene oxide);
Ethoxylated diamylphenol,
Ethoxylated octylphenol,
Ethoxylated nonylphenol,
Ethoxylated dinonylphenol,
Ethoxylated trinonylphenol,
Ethoxylated decylphenol,
Ethoxylated didecylphenol,
Ethoxylated undecylphenol,
Ethoxylated dodecylphenol,
Ethoxylated octyldecylphenol,
Ethoxylated diamylnaphthol,
Ethoxylated octylnaphthol,
Ethoxylated nonylnaphthol,
Ethoxylated dinonylnaphthol,
Ethoxylated trinonylnaphthol,
Ethoxylated octyldecylnaphthol,
Ethoxylated diamyl p-p' biphenol,
Ethoxylated octyl p-p' biphenol,
Ethoxylated nonyl p-p' biphenol,
Ethoxylated octyldecyl p-p' biphenol,
Ethoxylated dinonyl p-p' biphenol,
Polyoxyethylene oxypropylene glucoside oleate,
Glycerol monooleate, Sorbitan monolaurate,
Sorbitan monooleate,
Sorbitan trioleate,
Sorbitan sesquioleate,
Sorbitan partial fatty ester,
Ethylene glycol fatty acid ester,
mono- and diglycerides from the glycerosis of edible fats and oils,
mono- and diglycerides of fat-forming fatty acids,
Polyoxyethylene sorbitol beeswax derivitive,
Polyethylene glycol di(2-ethylhexoate) (Flexol 4GO),
Polyalkylene glycol derivitives (Flexol B-400),
Water-insoluble polyalkylene glycol liquids (Ucon "LB" fluids),
Chlorinated hydrocarbons,
Methylene chloride,
Trichloroethylene,
Perchloroethylene,
Monochlorobenzene,
Oil-soluble esters,
Diethylene glycol monobutyl ether acetate,
Benzene,
Gasoline,
Toluene,
Ethylbenzene,
Xylol (xylene),
Dimethyl naphthalene (mixed isomers),
Diethyl naphthalene,
Dipropyl naphthalene,
Dioctyl phthalate,
Water-insoluble alcohols,
2-Ethylhexanol,
Isodecanol,
Tetrahydropyran-2-methanol,
Di(iso-decyl)4,5-epoxy tetrahydrophthalate (Flexol PEP),
Di(2-ethyl-butyl) phthalate,
Ethylhexyl-decyl phthalate (mixed ester) (Flexol 810),
Didecyl phthalate (Flexol 10–10),
Di(2-ethylhexyl) isophthalate (Flexol 380),
Water-insoluble ethoxylated polyoxypropylene glycol derivitives,
Castor oil, The relative amounts of surfactant and synergist constituents employed in a given emulsifier or water-washable penetrant composition may vary considerably, depending on the "strength" or activity of the particular substances being used, so there are no set limits or proportional ranges which hold for all materials. However, I have found that in a large number of instances satisfactory gel-forming emulsifiers may be compounded by using one part synergist to about 2 to 5 parts surfactant. In some extreme cases, it may be possible to employ as little as one part surfactant to one part synergist, or as much as twenty parts surfactant to one part synergist. Such "balanced" surfactant/synergist detergent systems may then be combined with various inert extenders, oils, glycols, or other diluents, along with indicator dyes as required, to form compositions which are useful as inspection penetrants and emulsifiers.

Thus, by combining a surfactant (as defined herein) with a synergist (also as defined herein) to make a "balanced" detergent system, an unusual and useful effect is obtained, this being that the detergent system has the property of causing oil and water to mutually dissolve into one another to form clear solutions. Another important feature of "balanced" detergent mixtures is that the addition of water will cause the formation of gels which will remain stable even upon the addition of relatively large proportional amounts of water. That is to say, ordinary emulsifiers, particularly those which fall in the class of ionic, fatty acid soaps, "break" into emulsions, usually upon the addition of about 40 to 50% water, at most. Contrasted with this, gel-forming compositions utilizing "balanced" detergent systems may often exhibit broad gel ranges such that the gels remain stable up to more than 100% added water, and in some cases up to as much as 800% added water.

The balanced surfactant/synergist detergent systems are important, not only with respect to their feature of gel-formation, which yields high levels of flaw entrapment efficienty in penetrant system performance, as is described in the afore-mentioned patents and patent applications, but I have discovered that they have the additional unusual and advantageous property of exceptional sensitivity toward solvency inhibition under appropriate circumstances.

The various techniques of inhibiting or depressing the wash-removability of penetrant entrapments to be described are not limited to the so-called balanced surfactant/synergist type penetrants. I have discovered that certain other types of penetrant compositions also exhibit a feature of inversion of solubility at elevated temperatures of wash water, or in the presence of wash water containing high concentrations of solubility-inhibiting solutes. Accordingly, the methods described and claimed herein may be applied to any "solvency-sensitive" penetrant composition in which solubility or washability may be inhibited or depressed by the methods to be described.

For example, the so-called "slow-solubility" penetrant compositions described and claimed in my co-pending appln. Ser. No. 482,465, filed June 24, 1974, for "Enhanced Stability Water-Washable Penetrant Composition and Process", now U.S. Pat. No. 3,896,664, exhibit effects of solubility inversion or washability depression in a manner similar to the balanced surfactant/synergist type penetrants. It may be that the physical-chemical mechanisms may differ with different kinds of penetrant compositions, but the practical result of solubility inhibition is essentially the same with all penetrant compositions which are "solvency-sensitive".

I have discovered that the ability of a given emulsifiable penetrant to undergo the above-described emulsification transition, or of a given solvency-sensitive penetrant to dissolve in water, may be altered or inhibited to a pronounced degree in at least five different ways. Many water-washable penetrants, particularly those employing a balanced surfactant/synergist detergent system, are solute-sensitive, such that their solubility may be depressed or inhibited by adding a suitable solute to the wash water or to the penetrant itself. Some of the balanced-detergent-type water-washable penetrant materials, such as those employing ionic detergents or fatty acid soaps, are quite sensitive to the hardness of the wash water. My water-washable penetrant compositions employing balanced surfactant/synergist systems, and also my slow-solubility penetrant compositions, are temperature-sensitive, such that their solubility may be depressed or inhibited by raising the temperature of the wash water above some critical value.

Finally, some of my penetrant compositions employing balanced surfactant/synergist systems may be made to exhibit a depressed or inhibited solubility by allowing a relatively volatile solubility-producing constituent to evaporate from the film or coating of penetrant which is applied to test bodies.

For the purpose of this specification, it is important to differentiate between the effects of solubility and washability. I have discovered that solubility and washability in emulsifiable or slow-solubility penetrant materials are two separate and distinct features which may, for the most part, be controlled independently. In other words, I have found that it is possible to depress or inhibit solubility while retaining a satisfactory degree of washability under appropriate operating conditions. This invention contemplates the employment of one or more procedures whereby solubility is depressed or inhibited, while at the same time satisfactory washability may be effected by use of a suitable mechanical wash-water agitation, or spray-scrubber action, as will be described.

Now, to describe the various means whereby the solubilities of water-washable penetrants may be depressed or inhibited, I have discovered, firstly, that certain of the solvency-sensitive penetrant compositions, particularly those which employ anionic or cationic surfactant ingredients or fatty acid soaps, are sensitive to the "hardness" of the wash water. In certain of such emulsifiable compositions, the solubility may be depressed by a wash-water hardness no greater than 2 to 5 grains or so. In some of these water-washable penetrant compositions, the solubility is almost completely absent in 25 grain hard water.

It should be mentioned that a 25 grain hard water contains 25 grains per gallon of hardness-producing metal ions such as magnesium, calcium, iron, or manganese. Hard water may be softened by removal of these dissolved solutes, or ordinary soft water may be hardened by the addition of appropriate solutes. Although the usual industrial practice in water treatment is softening operation, or the removal of the "hard" solutes, it is quite practical to prepare water having a desired level of hardness by introducing the appropriate solute material, either batch-wise or by means of a siphon-suction arrangement which feeds a concentrated solution of hardness constituents into a stream of the water to be treated. Or, soft water may be fed through a "cake" of slightly soluble "hard" constituent material, whereby a desired hardness is picked up.

Referring now to FIG. 1, this figure illustrates the effect of an increasing hardness of wash water on the time required for wash-removal of a layer of balanced-detergent-type water-washable penetrant of the cationic, anionic, or fatty acid soap types. In conducting tests for the determination of the characteristic curves of FIG. 1, a Ceramic test block was employed as a test surface. Test blocks of this kind are described and claimed in my U.S. Pat. No. 3,164,006, and consist of unglazed ceramic surfaces on which there are multitudes of microscopic and sub-microscopic pits, pores, and cracks.

In use, a water-washable penetrant, preferably one with a fluorescent indicator dye, is applied to the Ceramic Block surface, and is drained off or wiped off so as to leave a thin layer of penetrant material. This coated test block is then immersed in a tray containing a quantity of wash water having a measured or known hardness, and the tray is rocked gently while the test surface is observed under ultraviolet irradiation. After a period of time, the uniform fluorescence of the test surface suddenly changes to a condition where fine porosity indications can be clearly seen. The time, in seconds, required for removal of the uniform surface fluorescence which obscures the fine indications is taken as the washing time for the particular test penetrant.

Curve 5 in FIG. 1 shows the variation in wash time with respect to wash water hardness for an emulsifier containing a simple ionic detergent. Curve 6 shows the variation in wash time with respect to wash water hardness for an emulsifier utilizing an ionic fatty acid soap in its detergent system. Many variations of these representative curves are obtainable with different combinations of ionic detergents and soap ingredients in the water-washable penetrant or emulsifier.

Secondly, I have found that certain water-washable penetrants, particularly those which employ balanced surfactant/synergist detergent systems, can be inhibited with respect to their solubility in water by the addition to the wash water of soluble materials such as various inorganic salts or organic compounds. Hexamethylenetetramine, for example, is highly soluble in water, and its presence as a solute in wash water tends to inhibit the wash-removability of water-washable penetrants.

Figure 2:
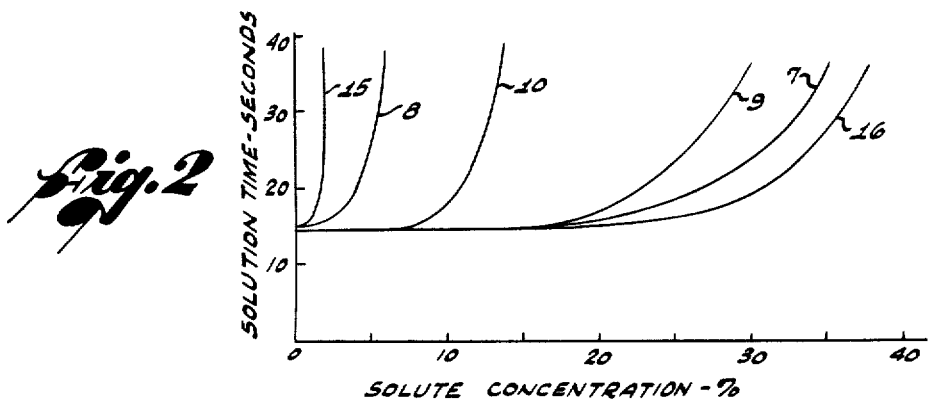
FIG. 2 is a graph in which the time for wash-removal of certain penetrant materials is plotted against the concentration of a dissolved solute in the wash water, or the concentration of a dissolved solute in the penetrant.

Referring now to FIG. 2, curve 7 of this figure illustrates the effect of increasing concentration of an organic solute, hexamethylenetetramine, on the washing time for a penetrant employing a balanced surfactant/synergist detergent system. Penetrants of the type used for this example are described and claimed in my co-pending application, Ser. No. 520,392, now issued U.S. Pat. No. 3,282,843. Here again, the determination of the times for wash removal are carried out using the Ceramic Block method as described above. Again, it is seen that as the concentration of the solute increases, the time required for wash removal of the penetrant increases. Similar characteristic curves are obtained for other solutes. Curve 8 illustrates the solubility inhibiting effect of sodium sulfate, while curve 9 illustrates the solubility inhibiting effect of potassium nitrate. With some solutes, such as potassium nitrate, the effect of solubility inhibition on water-washable penetrants may be relatively weak, so that pronounced inhibition is not achieved until the solute concentration approaches saturation, and of course, for solute materials which are weakly soluble, it may not be possible to achieve complete inhibition of solubility of the penetrant or emulsifier. Curve 10 illustrates the the solubility inhibiting effect of calcium acetate.

A wide range of solubility inhibiting ingredients are available, and virtually any water-soluble salt or organic material will act to depress the solubility of rhe solvency-sensitive water-washable penetrants, and the greater the concentration of the solute, the greater will be the effect of solubility inhibition. Among the many materials which I have tried, the following listing indicates a few materials which have been found to be particularly useful in this regard.

Sodium sulfate
Strontium chloride
Calcium acetate
Sodium acetate
Potassium nitrate
Ammonium carbonate
Magnesium sulfate
Urea Potassium dichromate
Polyvinyl pyrrolidone
Sodium chromate
Hexamethylenetetramine The selection of a suitable solubility-depressing solute for use in the wash water may be a matter of economics or of chemical compatibility with test bodies. For example, sodium sulfate in 10% concentration in water provides an effective inhibition of solubility, and permits a satisfactory spray-scrubber action. This particular solute material is quite inexpensive; however, due to the fact that the element sulfur is present in the compound, it may be found that it is undesirable to utilize the compound in connection with testing nickel alloy test bodies. This is for the reason that sulfur-bearing materials may cause intergranular corrosion effects on such alloys. In such cases, it may be found desirable to employ a more expensive solute material, such as calcium acetate, urea, or hexamethyenetetramine, which does not exhibit objectionable corrosion effects.

It will be understood that the above-identified solubility-inhibiting solutes may be incorporated in the wash water used in wash-removal of solvency-sensitive penetrants to a concentration which falls within the preferred range of from 5 to 35%. All of the above-identified solvency-inhibiting solutes exhibit an inhibition of solvency for applicable solvency-sensitive penetrants at concentrations between 5 and 35%.

I have found that it is possible to dissolve a suitable solute in the balanced surfactant/synergist-type water-washable penetrant itself, and thereby achieve the desired objective of depressing or inhibiting solubility in ordinary wash water. For this purpose, virtually any normally insoluble oily liquid, or any of the above-named synergists, may be added to and dissolved in the water-washable penetrant. For a given oily or synergist solute, and as its concentration in the water-washable penetrant is increased, a point will be reached where the solubility of the mixture undergoes a transition, being depressed eventually to the point where it appears to be nonexistent.

Referring again to FIG. 2, curve 15 shows the effect on the solubility of a nonionic-type water-washable penetrant of the addition of nonylphenol (synergist) as a solute. Curve 16 shows the effect on the solubility of the same penetrant of the addition of kerosene as an additive solute. In both cases, the penetrant containing the solute material retains its ability to maintain in clear solution substantial quantities of added water, even though the concentration of the solute is sufficient to effectively destroy the solubility of the mixture in water.

While there are many kinds of oils and mineral fractions which may be used as solutes in water-washable penetrants to effect a depression of their solubility in water, some solute materials present certain advantages over others, particularly where it is desired to achieve a given degree of solubility depression or inhibition by use of a minimum proportional quantity of additive material. In such cases, I have found it particularly advantageous to use as solute materials compositions of the types and character as described and claimed in my copending application Ser. No. 492,676, now U.S. Pat. No. 3,311,479. The method of this invention is not restricted to the use of any particular solute materials, since, as pointed out above, there are many kinds of solute materials which may be employed. The following listing indicates a few of the oily solute materials which have been found to be effective as solubility depressants.

Ethylene glycol di(2-ethyl-butyrate),
Triethylene glycol di(2-ethyl-butyrate),
Triethylene glycol di(2-ethyl-hexoate),
Polyethylene glycol di(2-ethyl-butyrate),
Propylene glycol di(2-ethyl-butyrate),
Polypropylene glycol di(2-ethyl-hexoate),
Didecyl adipate,
Di(2-ethyl-butyl) sebacate,
Didecyl sebacate,
Didecyl oxalate,
Di(2-ethylhexyl) adipate,
Di(2-ethylamyl) undecane-dicarboxylate,
Di(2-ethylheptyl) glutarate,
Dinonyl malonate,
Di(2-ethylhexyl) phenol,
Didecyl phenol,
Di (undecyl) phenol,
Di (dodecyl) phenol,
Octylphenol,
Nonylphenol,
Decylphenol,
Undecylphenol,
Dodecylphenol,
Di(2-ethylbutyl)4,5-epoxy-tetrahydrophthalate,
Di(2-ethylamyl)4,5-epoxy-tetrahydrophthalate,
Di(2-ethylhexyl)4,5-epoxy-tetrahydrophthalate,
Kerosene distillate fraction,
Diesel fuel distillate fraction,
Base oil-100 pale distillate fraction, In addition to the foregoing, any one or a combination of the previously listed synergist materials may be utilized as a solute in the balanced surfactant/synergist-type water-washable penetrant for the purpose of inhibiting its solubility in the water wash.

Fourthly, I have found that in solvency-sensitive penetrants and emulsifiers, particularly those described and claimed in my above-mentioned copending application Ser. No. 520,392, now U.S. Pat. No. 3,282,843, and appln. Ser. No. 497,058, now U.S. Pat. No. 3,349,041, the water-washability of the emulsifier or penetrant may be inhibited by raising the temperature of the wash water above some critical value. As the temperature of the wash water is raised, the rate at which water produces a solution of emulsification transition in the solvency-sensitive penetrant becomes progressively slower, until at some critical temperature the rate of solution reaches substantially a vanishing point.

Figure 3:
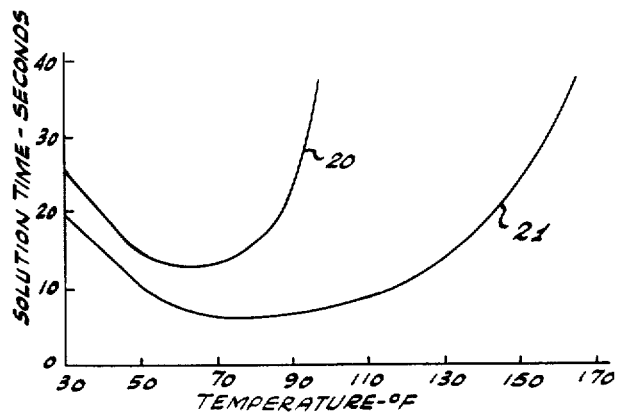
FIG. 3 is a graph in which the time for wash-removal of certain penetrant materials is plotted against the temperature of the wash water.

In certain of the balanced surfactant/synergist-type water-washable penetrant formulations, it has been noted that the onset of washability inhibition occurs at temperatures which are as low as 60° F. The effect of temperature on the solubility of two representative water-washable penetrants is illustrated in FIG. 3. Referring now to FIG. 3, curve 20 shows the variation in washing time as a function of wash water temperature for a water-washable penetrant employing a balanced surfactant/synergist detergent system in conjunction with a diesel fuel oily vehicle. Curve 21 shows the variation in washing time as a function of wash water temperature for a similar water-washable penetrant employing a refined kerosene as the oily vehicle.

In the case of the slow-solubility penetrant compositions described and claimed in my above-mentioned U.S. Pat. No. 3,896,664, the onset of solubility depression usually occurs at considerably elevated temperatures of the wash water, in some cases near the boiling point of water.

For all of the solvency-sensitive penetrants which have been described, the onset of washability-inhibition or solvency depression occurs somewhere in the range of about 90° F. or above, up to the boiling point of water. It will be understood, therefore, that the water-wash remover is utilized within the above-indicated range of elevated temperatures, and with sufficient agitation or relative movement between the remover liquid and the penetrant-treated test surface so as to remove the excess penetrant from said surface.

The above-described features of washability have been set forth with respect to a gentle flow type of washing, where the wash water is allowed to flow gently over a test surface coated with the water-washable penetrant being evaluated for its washability. Alternatively, the penetrant-coated test surface may be immersed in a tray of wash medium, and the tray may be rocked gently, as described above, and the rate at which wash-removal takes place may be observed. In any case, the critical condition of solute concentration and/or temperature of the wash water above which washability diminishes or ceases may be readily determined.

I have discovered that the solvency-sensitive water-washable penetrants which have been inhibited in the above-described ways may be successfully wash-removed from test surfaces by employing a certain degree of mechanical agitation, either of the test part or of the wash water. In effect, the agitation accelerates any slight residual tendency toward solubility or emulsifiability of the inhibited penetrant material.

It will be understood that techniques of spray removal of surface soil and oily residues from surfaces are old in the art. In addition, it will be understood that inspection penetrant processes, employing the steps of applying a water-washable penetrant to test surfaces, treating the test surfaces by washing with a water-wash remover to effect removal of surface penetrant, and inspecting the washed test surfaces for the presence of entrapments of penetrant in surface defects, are also old in the art. However, this invention contemplates an improvement in such processes wherein certain of the appropriate types of solvency-sensitive penetrants, as described herein, are caused to have their solvency inhibited in the presence of a water-wash remover to a point of substantial insolubility, except in the presence of mechanical agitation of or within the water-wash remover.

In my copending application, Ser. No. 464,360, now U.S. Pat. No. 3,422,670, I have described and claimed a method and means for wash removal of normally insoluble oily penetrants by means of normally inactive emulsifiers, whereby the emulsifying action of the "inactive" emulsifier is accelerated by means of mechanical agitation. A similar effect takes place in the process of the present invention, except that in the present case, the wash medium is water, or it is water containing a dissolved solute, or it is at a temperature above a critical point where washability inhibition is initiated, rather than being an "inactive emulsifier".

The mechanical agitation which is employed in connection with the compositions of the present invention, as well as that employed in the abovementioned invention of appln. Ser. No. 464,360, may be introduced in several ways; i.e., by mechanical vibration or motion of the test part, by sonic or ultrasonic vibration introduced into the wash water or the test part, by turbulence due to a pressurized stream of wash water, by air-agitation of the wash water, or by a pressure spray of the wash water. If sonic or ultrasonic vibration is employed to provide the desired mechanical agitation, care should be taken to insure that the amplitude of such vibration, or its total energy, should be sufficient to remove surface penetrant, but less than that required to drive penetrant entrapments out of small surface flaws. It will be understood that the various techniques of applying mechanical agitation are, in themselves, old in the art, and are presented here merely by way of illustrating suitable means for "scrubber-removal" of the solubility-inhibited compositions of the invention.

Figure 4:
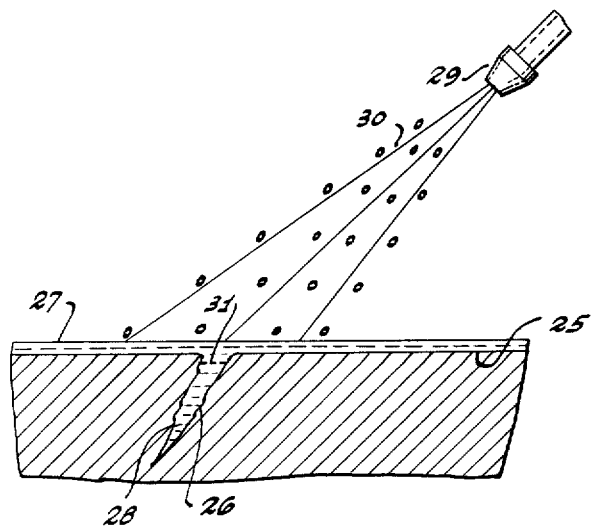
FIG. 4 is an illustration in cross-section of an adaptation of a removal technique suitable for use in connection with the invention, utilizing a spray of wash medium to remove an insolubilized penetrant from the surface of a test body.

Referring now to FIG. 4, this figure illustrates one adaptation of the process of this invention in which a spray of wash water, either with a dissolved solute or at a temperature above a critical point of washability inhibition, is directed onto a test surface which has been coated with a water-washable penetrant. A test surface 25 in which there is a surface flaw 26 is coated with a layer of solvency-sensitive water-washable penetrant 27. The penetrant liquid, containing an indicator dye, enters the surface flaw 26 to form an entrapment of liquid 28.

A spray nozzle 29 is positioned so as to direct a spray of treated wash water 30 onto the test surface 25 so as to remove the surface layer of penetrant 27. Either the penetrant of layer 27 or the water of the spray 30 is treated by one or more of the procedures which are described above so that an inhibition of solubility is initiated. Despite the inhibition of solubility of the layer 27, due the treatment described above, the mechanical agitation of the water spray 30 is such that the layer of surface penetrant 27 is removed. However, the entrapment 28 of the penetrant liquid is substantially unaffected by the spray because the droplets of the spray 30 are relatively large, and the mere contact of the wash water with the penetrant entrapment will not cause it to dissolve. Thus, the entrapment is effeciently retained in the surface flaw 26 so that the surface flaw is almost completely filled with the penetrant liquid, as indicated by line 31. A prolonged washing with the treated spray 30 has little or no effect on the entrapment 28, even though the surface layer of penetrant 27 is completely removed.

Under properly selected conditions of solute content in the wash water, wash water temperature, or both, it is found that with a mechanical agitation, the water-washable penetrant or emulsified penetrant, as the case may be, will be selectively removed from the surfaces of test parts, while penetrant entrapments in surface flaws will be inhibited in their wash removal. Accordingly, and by the combination of inhibition of solubility and mechanical agitation during washing, the effective stability of the penetrant entrapments is greatly enhanced, and a greatly increased latitude in the time of washing is achieved.

In practice, process steps which are carried out in connection with the solubility-inhibited compositions of the present invention are carried out along with a series of other steps, most of which are also conventional. For example, the various essential steps involved in an inspection penetrant process employing a water-washable penetrant (1) penetrant application, (2) removal of surface penetrant by washing, and (3) inspection. Usually, one or more steps of pre-cleaning, etching, etc., precede the step of penetrant application, and often the steps of developer application and drying precede the final step of inspection for surface flaw indications.

It will be seen from the foregoing description that I have discovered a new and novel method of wash-removal of water-washable penetrants and emulsifiers from the surfaces of test bodies, which method provides an increase in latitude in washing and an improved level of flaw entrapment efficiency in penetrant inspection processes employing water-washable penetrants or emulsified oily penetrants.

I claim:

1. In a process of penetrant inspection of test parts for surface discontinuities, comprising the steps of applying a solvency-sensitive water-washable dyed penetrant to a test surface, treating said test surface by washing with a water-wash remover to effect removal of excess surface penetrant, and inspecting said test surface for the presence of penetrant entrapment indications, the improvement that avoids solution-removal of penetrant entrapments in crack defects which comprises; raising the temperature of said water-wash remover to above the point of solvency transition of said dyed penetrant, said temperature of solvency transition being within the range of about 90° F. up to the boiling point of water, and applying said water-wash remover with sufficient relative movement between the remover and the penetrant-treated test surface to remove the excess penetrant from said surface.

2. In a process of penetrant inspection of test parts for surface discontinuities, comprising the steps of applying a solvency-sensitive water-washable dyed penetrant to a test surface, treating said test surface by washing with a water-wash remover to effect removal of excess surface penetrant, and inspecting said test surface for the presence of penetrant entrapment indications, the improvement that avoids solution-removal of penetrant entrapments in crack defects which comprises: dissolving a solubility-inhibiting solute in said water-wash remover to a concentration within the range of about 5 to 35%, sufficient to inhibit the solubility of said dyed penetrant, said solubility-inhibiting solute being at least one member selected from the group consisting of Sodium sulfate,
Calcium sulfate,
Calcium acetate,
Potassium nitrate,
Magnesium sulfate,
Potassium dichromate,
Sodium chromate, and
Strontium chloride,
Lead acetate,
Sodium acetate,
Ammonium carbonate,
Urea,
Polyvinyl pyrrolidone,
Hexamethylenetetramine, and applying said water-wash remover with sufficient relative movement between the remover and the penetrant-treated test surface to remove the excess penetrant from said surface.

* * * * *